United States Patent [19]

Bennison

[11] Patent Number: 4,580,226

[45] Date of Patent: Apr. 1, 1986

[54] RANDOM SAMPLING SYSTEM

[75] Inventor: Roger Bennison, Roanoke, Va.

[73] Assignees: Sanford H. Robbins, Wilton, Conn.; Edward F. Keating, Scarsdale, N.Y.

[21] Appl. No.: 597,364

[22] Filed: Apr. 6, 1984

[51] Int. Cl.[4] .................. G06F 15/46; G06F 15/20
[52] U.S. Cl. ............................ 364/478; 364/552; 364/554
[58] Field of Search .............. 364/478, 552, 554, 717; 328/151; 331/78

[56] References Cited

U.S. PATENT DOCUMENTS

| | | | |
|---|---|---|---|
| 3,151,237 | 9/1964 | Hrabak | 364/552 |
| 3,222,504 | 12/1965 | Arnold et al. | 364/552 |
| 3,274,377 | 9/1966 | Morison | 364/552 |
| 3,944,051 | 3/1976 | Weaver | 364/552 |
| 3,952,185 | 4/1976 | Stultz et al. | 364/552 |
| 4,045,659 | 8/1977 | Akagawa et al. | 364/554 X |
| 4,115,867 | 9/1978 | Vladimirov et al. | 364/554 X |
| 4,136,396 | 1/1979 | Hansford | 364/552 X |
| 4,142,238 | 2/1979 | Brandt et al. | 364/552 |
| 4,187,545 | 2/1980 | Wallace et al. | 364/552 X |
| 4,205,383 | 5/1980 | Bakanovich et al. | 364/554 |
| 4,237,539 | 12/1980 | Piovoso et al. | 364/552 |
| 4,275,451 | 6/1981 | Balzarini et al. | 364/478 X |
| 4,344,146 | 8/1982 | Davis, Jr. et al. | 364/552 |
| 4,363,105 | 12/1982 | Plassmeier | 364/580 |
| 4,472,784 | 9/1984 | Blachman | 364/554 |

*Primary Examiner*—Joseph Ruggiero
*Attorney, Agent, or Firm*—Roland T. Bryan

[57] ABSTRACT

Apparatus and process for randomly selecting articles for removal from an advancing series thereof. An operator chooses the total number of a batch of the articles from which the random selection is to be taken, as well as the total number of samples of the articles to be taken from the batch. A series of random numbers, each representing an incremental advancement of the series of articles, is developed when a reset button is actuated by the operator which interrupts a very long sequence of numbers held in the memory of a micro-computer, thereby establishing a starting point. A sensor senses the articles as they pass a predetermined station, and those articles are removed from the advancing series which relate in the sequence to each randomly generated number. Information is displayed which relates to the number of the batch, the number of samples, and the number of articles still to pass the predetermined station immediately prior to the next article scheduled for removal. The apparatus and process can also be used to remove random samples from an advancing flow of fungible material.

22 Claims, 4 Drawing Figures

RANDOM SAMPLING SYSTEM

BACKGROUND OF THE INVENTION

1. Field of the Invention

The present invention relates generally to a new and improved process and apparatus for randomly selecting any preselected number of samples of an item from any preselected batch or population number for that item. The item being monitored may be any item which is being produced in quantity, the level of quality of which it is desirable to inspect from time to time.

For purposes of the disclosure herein, the term "batch" or "population" is taken to mean the group of all the items that fit a particular description, for example, a production run; the term "sample" is taken to mean a number of objects chosen for a given batch or population as representative of the entire group; and "random sample" is a sample in which every item in the batch or population has an equal chance of being chosen for the sample.

2. Description of the Prior Art

It is customary in many industries utilizing mass production techniques to remove, at intervals, items being produced as they advance along the assembly line. These items are then examined to determine their fitness for sale and consumption. In the ideal world, each item would be examined. However, such 100 percent examination is a practical or commercial impossibility since the time and, therefore, cost involved would not permit it. Furthermore, it is not necessary to perform such a total examination in any event, since, statistically, it is very likely that if a proper sampling is taken, any problems present will appear. And if a problem with the production item appears in quantities that are greater than a permissible level, that is a clear indication that some action must be taken with the entire production run in order to alleviate the problem.

Such sampling is of particular importance in the food and beverage processing industries to assure that items intended for human consumption are fit for such consumption. However, various sampling techniques have been used in virtually every industry in which relatively large numbers of items are produced and in which it would be impractical or impossible to inspect every single item.

However, not only is it necessary that a sampling of items be made in order to determine the quality of the vast majority of the items in the entire batch or population from which the inspection is taken. Indeed, it is necessary that the sampling be random in order for it to be effective. It will be appreciated that machinery operates in a repetitive fashion and that while this is a desirable characteristic for many functions, it is an undesirable characteristic when the goal is to obtain randomness of operation. Specifically, it is possible that a selection of items at uniformly spaced intervals during a production run could establish a pattern which would closely match a pattern in the population of the items such that an accurate representation of the finished product is not obtained. For example, most filling and packaging systems operate on a fixed scale basis such that a uniformly spaced selection of sample items could result in obtaining successive sample items which were filled by the same station of a filling machine or closed by the same station of a sealing machine. By so dwelling on one aspect of the production run, a problem which might actually exist at some other station of the machinery might be overlooked.

The most pertinent prior art known to the inventor will now be discussed. The U.S. patent to Hrabak, U.S. Pat. No. 3,151,237 issued Sept. 29, 1964, is representative of that class of inventions in the prior art which serves to glean an amount of a variable for controlling the quality of that specific variable. The patent is not concerned with random number selection, but discloses a statistical quality control system for determining the statistical distribution of certain quality characteristics of an article of manufacture.

The U.S. patent to Wallace et al., U.S. Pat. No. 4,187,545 issued Feb. 5, 1980, is representative of that class of prior art inventions which serve to compare an article of manufacture being produced with an established one. If there is a problem, that problem is corrected or the item causing the problem is ejected. In the Wallace patent, apparatus is disclosed for determining the orientation of articles advancing along a conveyor, correcting them if they are not properly oriented or ejecting them for another attempt. As with the Hrabak patent, there is no consideration or discussion in the Wallace patent of random number selection.

The U.S. patent to Weaver, U.S. Pat. No. 3,944,051 issued Mar. 16, 1976 is the prior art known to the inventor which is closest in concept to the invention. Weaver utilizes a pair of counters which operate in conjunction with a switching mechanism to achieve some degree of randomness. However, unlike the system employed in the present invention, Weaver seeks to achieve a result in which the random selection is spread evenly across the entire production run. That is, according to the system of Weaver, only one sample is chosen out of a predetermined batch size which will result in a preselected whole number percentage at the end of a production run. On each occasion that the first counter recycles, for example, after the passage of every 50 or 100 articles of the production run, a new batch is begun. Although the Weaver system does achieve a certain level of randomness, it does not achieve that degree of randomness which modern industry, particularly the food processing industry, considers necessary in order to provide the quality of product properly demanded by today's consumer.

With proper deference being given to the aforesaid patents, each of which, on its face, discloses an advance in the state-of-the-art as of the date when each respective patent was granted, nonetheless, the present invention is deemed to be a considerable improvement over such known devices. Indeed, it was with recognition of the need and the state of the prior art that the present invention was conceived and has now been reduced to practice.

SUMMARY OF THE INVENTION

To this end, there is disclosed herein apparatus and a process for randomly selecting articles for removal from an advancing series thereof. An operator chooses the total number of a batch of the articles from which the random selection is to be taken, as well as the total number of samples of the articles to be taken from the batch. A series of random numbers, each representing an incremental advancement of the series of articles, is developed when a reset button is activated by the operator which interrupts a very long sequence of numbers held in the memory of a micro-computer, thereby establishing a starting point. A sensor detects the articles as they pass a predetermined station, and those articles are removed from the advancing series which relate in the sequence to each randomly generated number. Information is displayed which relates to the number of the batch, the number of samples and the number of articles still to pass the predetermined station immediately prior to the next article scheduled for removal. The apparatus and process can also be used to remove random samples from an advancing flow of fungible material.

Prior to describing the invention itself in further detail, it is considered as helpful, first, to discuss in general terms the concepts of batch size, sample size, randomness, and random number generation.

At the outset, the term "batch" has previously been defined as the group of all items which fit a particular description, as, for example, a production run. In the extreme, for any manufacturing facility making a particular product, the ultimate batch would be the total number of that product which has ever been made or even will ever be made at that facility. However, for quality control purposes, it would be impossible to consider anything more than a very small percentage within that full size batch. Specifically, quality control requires that the information as to quality of the product become available sufficiently quickly that such knowledge can influence the outcome of the production process. Thus, the user will want to so define a batch to be examined as a number of articles of sufficient size as to establish a meaningful result, yet not so large that the response time is unacceptably long.

When one is establishing a quality control procedure, there are predetermined and well-known mathematical relationships which allow one to specify what percentage of the product is defective according to some predetermined test. Once the percentage of acceptable units is defined, a sampling procedure can be derived which establishes a sample percentage. For example, to take an over-simplified instance, if it is desired to obtain no more than one percent defective product to be shipped out to a customer, 125 samples would be randomly selected from batches of 1500 articles, subjected to testing, and, of this group, no more than three failures would be considered as acceptable. See Standard Tables, MIL-STD-105D, quoted from Quality Control Handbook, Third Edition, J. M. Juran, Editor, McGraw-Hill Book Company, ISBN 0-07-033175-8.

Of course, it must be appreciated that randomness is not an abolute concept; rather it is an ideal to be approached. The closer one approaches the ideal, however, generally the greater the cost. The present invention is successful in obtaining a very high degree of randomness at moderate cost.

Now, if a large number of "random numbers" are generated, the randomness of their selection can be gauged by reference to "perfect randomness". Taking numbers from 0 to 9 for simplicity, if they are generated at random, then any digit, such as "3", will occur at a rate which gives a total of 1/10 or 10% of the total of numbers generated. In other words, each digit in the range of 0-9 has an equal (10%) probability of occurring. A measure of this would be the expression:

$$\sum_{i=o}^{9} \frac{[o(i) - e(i)]^2}{e(i)}$$

where o equals actual occurrence of digit i and e equals expected occurrence of digit i. Normally accepted is the criterion that this expression must work out to a number greater than 2.7 and less than 19.0. See Kennedy, Michael and Solomon, Martin B., *Eight Statement PL/C (PL/ZERO) plus PL/ONE*, Prentice-Hall, Inc. 1972, ISBN 0-13-246827-1. This result can be seen graphically by plotting the sequence 0 through 9 on the ordinate or x-axis and the number of times a particular digit is selected on the abscissa or y-axis. If imaginary dice are rolled for a very long time, and the results are plotted, the result should be a flat or horizontal distribution curve because there is an equal likelihood that any of those digits will be chosen after making many, many selections.

The approach of the inventor in arriving at the random samples of the present invention has been to aim for independence from outside influences and, as nearly as practical, achieve the die-rolling ideal.

In practical terms, however, it is very difficult to obtain truly random numbers in a simple electronic machine. Very few electrical phenomena are random; they usually run the risk of being periodic at some time or another. For this reason, it is usual to deal with "pseudo-random" numbers. These are numbers taken from a very long sequence which can be obtained by arithmetic operations. One example is to take ascending powers of 75, modulo 65537, subtract one, then divide by 65536. This procedure yields a series of numbers in the range of $0 \leq N < 1$ which can then be used to multiply by the batch size to obtain suitable sample numbers. The following example provides a partial representation (that is, only through the fifth power of 75) of this procedure.

| Powers of 75 | Modulo 65537 | $-1 \div 65536$ | Sample Numbers In a Batch of 500 |
|---|---|---|---|
| $(75)^1 = 75$ | 00075 | 0.0011291 | 1 |
| $(75)^2 = 5625$ | 05625 | 0.0858154 | 43 |
| $(75)^3 = 421875$ | 28653 | 0.4371948 | 219 |
| $(75)^4 = 31640625$ | 51791 | 0.7902526 | 395 |
| $(75)^5 = 2373046875$ | 17642 | 0.2691803 | 135 |

To complete this example, one would continue on for 65536 total numbers in a series. The number 65536 is chosen because it is the 16th power of two, a convenient number utilized by electronic hardware for computing operations. In further explanation, the word "modulo" is a mathematical term which simply denotes a continuing series of subtractions until a remainder is reached which is smaller in magnitude than the divisor. Thus the numbers in the second column represent those remainders from the first column number which, following successive subtractions of the number 65537 from the first column number, is less than the number 65537. Of course, in the first two instances, there can be no such remainder since the first column number is too small; hence the raw first column one number is merely transferred to the second column. As a further assurance of randomness, the number 65537 is chosen to be one digit larger than 65536 (i.e. $2^{16}$). As such, it is a prime number, and it is highly unlikely that any resulting remainder would produce a regularly repeatable number. Then for the operation as presented in the third column of the example, the number one is subtracted from the second column number in order to assure that all numbers obtained are within the range of the computer. In this regard, it will be recalled that the number 65536 is $2^{16}$, a convenient number for electronic hardware.

Having thus employed computing power to obtain such a large series of numbers, one can enter the sequence at any point to obtain a suitable group of numbers. Of course, as can be readily imagined, such a technique was impractical until the advent of relatively inexpensive micro-computers. Now, if one uses one random event to select a starting point in the sequence, such as the length of time a person presses the reset button, then the sequence of numbers obtained will appear to be random and will be guaranteed to maintain acceptable randomness of selection.

The concept of the random sampler of the invention, then, is generally as follows. A microprocessor waits for a reset button to be pressed. In the meantime it is continuously cycling through, or at least has available in it, the random number calculation described above. When the button is pressed, the front panel displays are examined to discover what number of samples is required and from what size of batch. Having determined these data, the micro-processor picks up wherever it happened to be in the number sequence when the button was released, and starts to list the desired samples in its memory.

Since a pseudo-random number is usually a multi-digit decimal in the range $0<N<1$, the micro-processor multiplies the first number encountered by the number in the batch to obtain the number of a sample to be taken. The resulting number will of course be the nearest whole number in the range 0→batch.

This procedure is repeated, again and again, until enough sample numbers have been accumulated in memory, whereupon the numbers are sorted into ascending order. When this is complete, the microprocessor begins to count items until the first sample number is reached, at which point the package is ejected from the conveyor. The next sample number is then fetched from memory and the micro-processor keeps counting items until that number is reached. This process continues until all the desired samples have been taken, when the micro-processor can either being another batch, or cease until reset by the operator, according to how it was programmed.

Thus, the present sampler can perform in the same way as the Weaver patent, discussed previously, by choosing one sample out of a batch of 50, or can be very much more satisfactory from a statistical point of view in choosing 79 samples from a batch of 4973 (for example), or any other number of samples from any other batch size, within the limits of the design. In addition, of course, the present sampler is guaranteed to be acceptably random whatever conditions prevail on the conveyor.

Still another benefit can be realized by users of the invention. In this regard, it is noteworthy that many large volume producers of consumer goods require their suppliers to include a "master sample" in shipments which is checked for defects prior to the acceptance of the shipment. Typically, a box of 100 cans or bottles or caps is separately boxed in a truckload of 100,000. This "master sample" is collected manually by the producer according to preestablished instructions from the suppliers. it is an expensive system and one which is difficult to administer. The new random sampler can easily perform this task automatically and set aside the "master sample" on an organized, economical and accurate basis. Thus, both the producer and the supplier benefit from the invention and can pass those benefits, including savings reflected in lower prices, along to the consumer.

Other and further features, objects, advantages, and benefits of the invention will become apparent from the following description taken in conjunction with the following drawings. It is to be understood that both the foregoing general description and the following detailed description are exemplary and explanatory but are not restrictive of the invention. The accompanying drawings which are incorporated in and constitute a part of this invention, illustrate one embodiment of the invention and, together with the description, serve to explain the principles of the invention.

DETAILED DESCRIPTION OF THE DRAWINGS

DESCRIPTION OF THE PREFERRED EMBODIMENT

Figure 1:
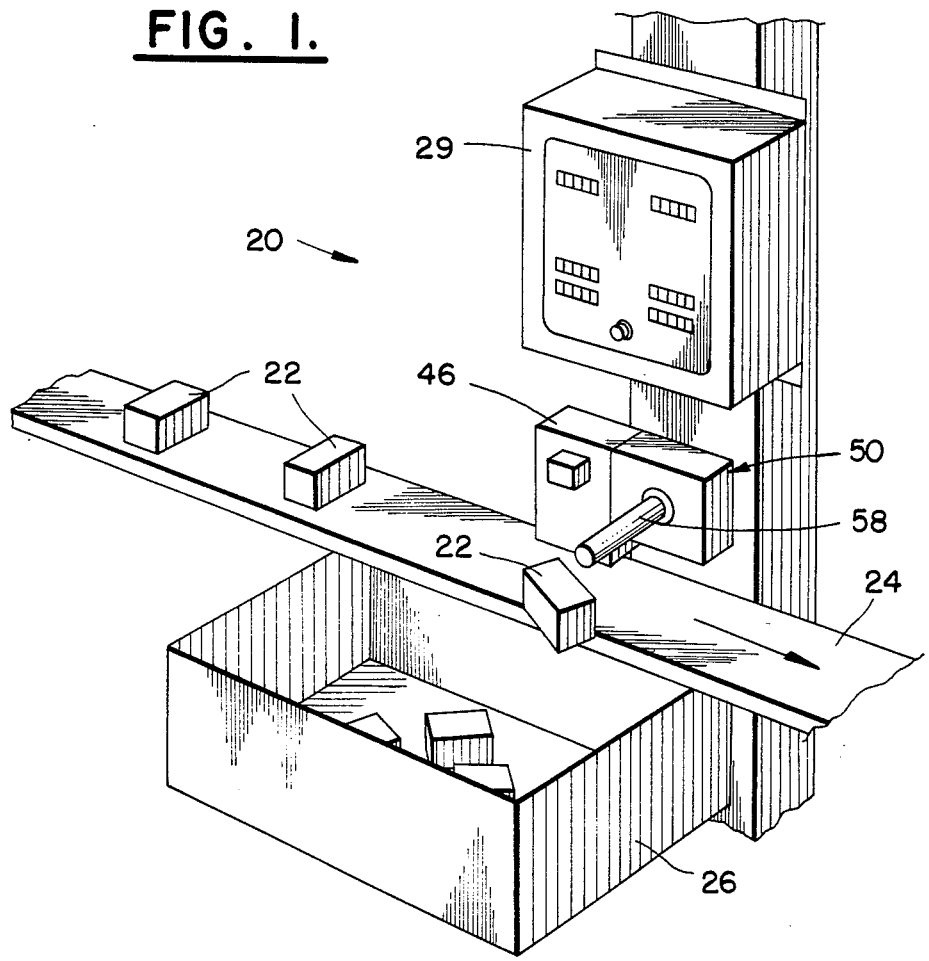
FIG. 1 is a perspective view of a sampling station alongside an advancing conveyor which utilizes the random sampling process and apparatus of the present invention.

Refer now to the drawings, and initially to FIG. 1 which generally illustrates a random sampler 20 which embodies the principles of the present invention.

In accordance with the invention, apparatus is disclosed for randomly selecting articles for removal from an advancing series thereof as they pass a predetermined station comprising: first selection means operable for establishing the total number of a batch of the articles from which the random selection is to be taken; second selection means operable for establishing the total number of samples of the articles to be taken from the batch; a number generator providing a very long sequence of numbers; reset means operable to externally interrupt said number generator to establish a starting point in the sequence of numbers provided by said number generator; developing means responsive to operation of said reset means for developing a series of random numbers within the magnitude of the batch size as established by said first selection means, each random number representing an incremental advancement of the series of articles; random access memory means for storing in memory the series of numbers developed by said developing means; sensor means for sensing the presence of each of the articles as it passes a predetermined station; and selection means operable for removing from the advancing series of articles those articles which relate in the sequence to each randomly generated number stored within said random access memory means.

Figure 2:
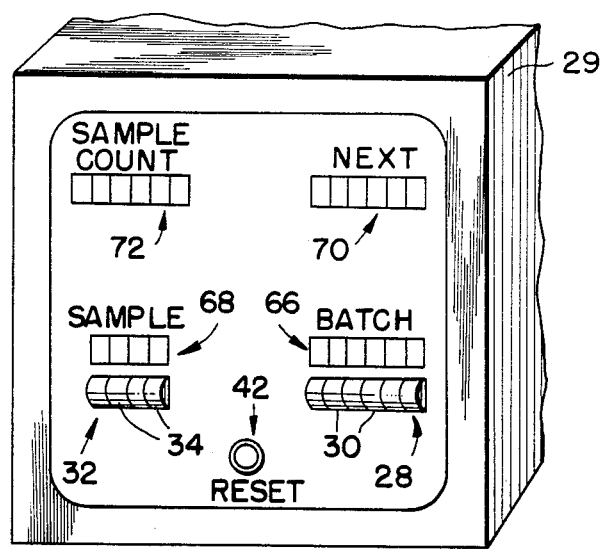
FIG. 2 is an enlarged perspective view of the front panel illustrated in FIG. 1 illustrating its components in detail.
Figure 3:
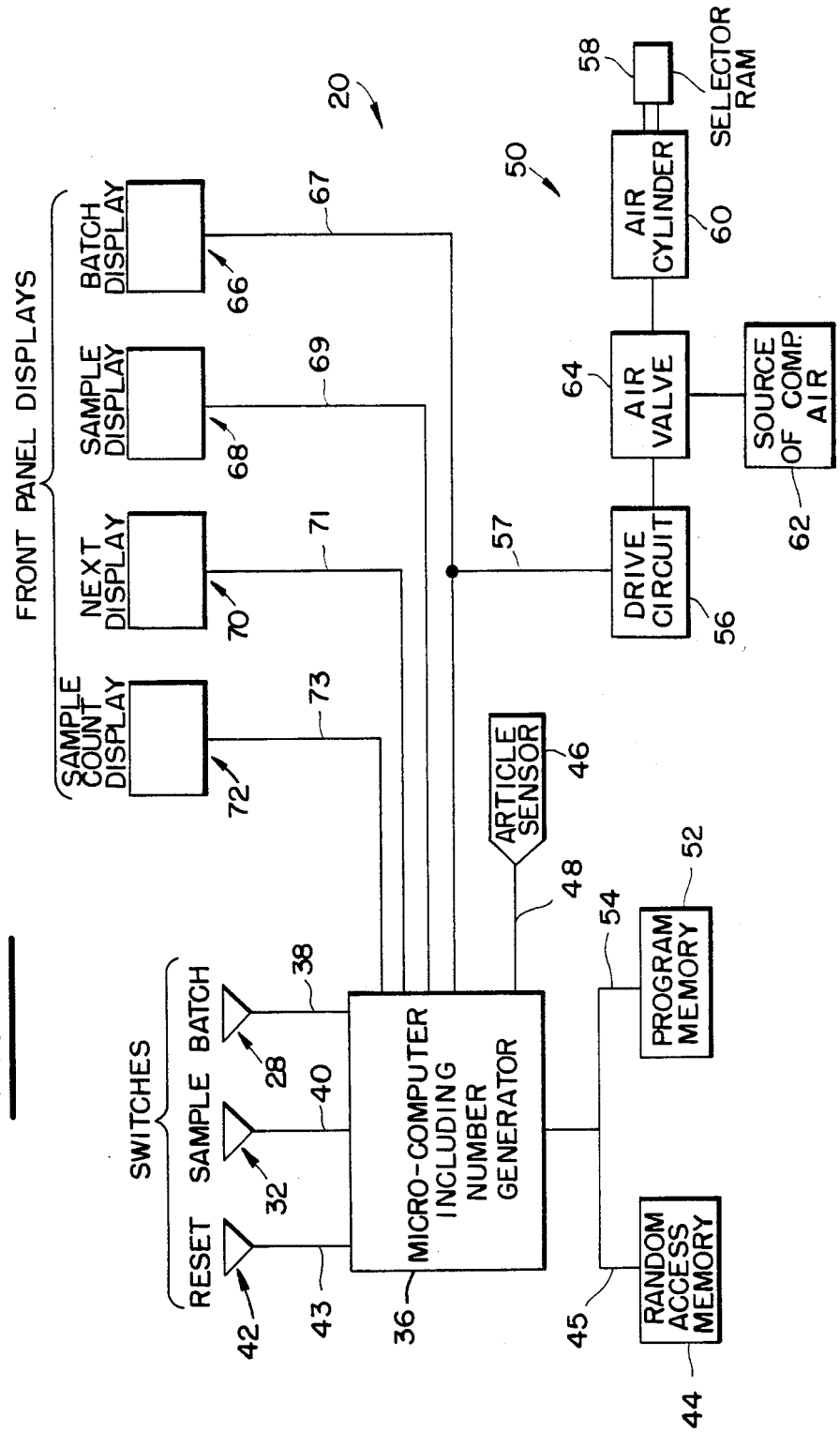
FIG. 3 is an operational schematic drawing which serves to illustrate the operation of one embodiment of the present invention.

As embodied herein, with particular reference to FIGS. 1-3, a random sampler 20 is used in conjunction with a series of articles 22 as they advance in any customary fashion on a suitable conveyor 24. For purposes of the invention, it makes no difference whether the conveyor remains stationary and the articles 22 are moved relative to the conveyor, or if the conveyor itself is moved and the articles 22 advance therewith. What is important is that the articles 22 are moved relative to a sampling station as represented by a sample collection container 26 positioned adjacent to the conveyor 24 in some suitable manner and at some suitable location so as to receive therein selected ones of the articles 22.

As seen particularly well in FIG. 2, a first selector 28 provided in the front panel of a main control unit 29 serves to establish the total number of a batch of the articles 22 from which the random selection is to be taken. The first selector 28 can be any suitable device for this purpose, but is illustrated in FIG. 2 as being a plurality of thumbwheel switches 30, each switch representing one digit of a multidigit number. The operator of the random sampler 20 sets the first selector 28 to reflect the total number of the batch of the articles 22 from which the random selection is to be taken.

In a similar fashion, a second selector 32 is also located in the front panel of the control unit 29 and serves to establish the total number of samples of the articles 22 which are to be taken from the batch as determined by the first selector 28. Again, it is the choice of the operator to determine the number of samples to be taken and the selector 32 is suitable provided with a plurality of thumbwheel switches 34, each of which represents one digit of a multidigit number.

Thus, the operator uses well-known mathematical relationships and standards of quality control to determine what number of samples is desired from a predetermined batch size and this information is entered into the random sampler 20 prior to its operation.

With particular attention now to FIG. 3, the random sampler 20 is provided with a micro-computer 36 which is illustrated, for sake of simplicity, as a single component. In actual fact, the micro-computer 36 may be an interconnected group of integrated circuits including a number generator and an interface between passive elements for receiving information and active elements for performing physical operations. One typical example of the micro-computer 36 might be the combination of a Z80A-CPU micro-processor integrated circuit and a Z80A-PIO programmable input-output integrated circuit, both manufactured and sold by Zilog Inc., of Campbell, Calif.

As is seen in FIG. 3, the information provided by the first and second selectors 28 and 32 is provided to the micro-computer 36 via electrical leads 38 and 40, respectively.

In furthering the operation of the random sampler 20, the micro-computer, as previously explained, includes a number generator which provides a very long sequence of numbers. The numbers of the sequence may be generated in accordance with the example indicated above and may be that series of numbers obtained in the third column of the example provided above. As previously explained, it is preferable that these numbers be in the range of 0–1, so that, when multiplied by the size of the batch as determined by the operator, the multiplicand is a whole number no greater than the predetermined size of the batch.

The element of the random sampler 20 which actually serves to initiate its operation is a reset button 42, also located in the front panel of the main control unit 29 (see FIGS. 2 and 3), which, via electrical lead 43 communicates with the micro-computer 36. By operating the reset button 42, the number generator portion of the micro-computer 36 is externally interrupted to thereby establish a starting point in a sequence of the numbers provided by the number generator. The reset button 42 is actuated whenever desired by the operator. However, it will be appreciated that while the button 42 can be operated by a human being, it can also be operated by any other suitable external force or mechanism. However, if the outside force is provided by some external mechanism, whether it be mechanical, electrical, chemical, or some other energy form, it may lose some of the random behavior which is assured by use of a living being. Thus, the reset button 42 serves to establish a haphazard starting point in a sequence of numbers as presented in the third column of the example provided above.

The micro-computer 36 also includes a development section which is responsive to operation of the reset button 42 for developing a series of random numbers within the magnitude of the batch size as established by the first selector 28. Each of the random numbers represents an incremental advancement of the series of articles 22. That is, each random number represents one of the sample articles chosen to be removed from the conveyor 24; and when the random numbers are arranged in sequence from lowest to highest, each random number represents the next sample article chosen to be removed from the conveyor. The development section, then, represents that portion of the micro-computer 36 which multiplies the numbers in the third column of the above described example by the number chosen for the batch in order to arrive at the numbers in the fourth column of the same example.

The random sampler 20 also includes a random access memory 44 for storing the series of numbers developed by the development section of the micro-computer 36. The memory 44 serves to store transient data as and when it is generated in the course of operation of the sampler 20. One typical example of memory 44 is the type MM 5290 integrated circuit manufactured by National Semiconductor Corporation of Sunnyvale, Calif. As utilized in the present invention, the memory 44 is preferably bi-directional, that is, it can receive, store, and retransmit information. Also, as utilized in the present invention, the memory 44 supplements the limited data storage capacity of the micro-computer 36 to which it is electrically connected as by lead 45, specifically, the memory 44 provides the micro-computer 36 with the list of random numbers as described above.

A suitable sensing device 46, such as a proximity sensor, one example being Type 871C, manufactured by Allen-Bradley of Milwaukee, Wis. operates to sense the presence of each of the articles 22 as it passes a sample collection container 26. As illustrated in FIG. 3, the sensor 46 is electrically connected to the micro-computer 36 as by electrical lead 48 to thereby convey information to the micro-computer as to each article 22 which has passed the station represented by the sample collection container 26.

The random sampler 20 also includes a selection mechanism which is operable for removing from the advancing series of articles 22 those articles which relate in the sequence to each of the randomly generated numbers stored within the random access memory 44. To this end, a program memory 52 serves to instruct the micro-computer 36 in the operation of the selection mechanism 50. In actual fact, the program memory 52 is a list of instructions for the micro-computer. A typical integrated circuit which operates in a manner necessary to support operation of the invention in this regard is designated the type "2716" manufactured by Intel Corporation of Santa Clara, Calif. While "2716" is a chip of integrated circuitry which is purchased blank, it is programmed with information provided by the manufacturer or user which enables it to control the operation of the micro-computer 36.

In this application, it reads the information set into the thumbwheel switches 30 and 34 by the operator, governs the action of the number generator (one of the functions of the micro-computer 36), and organizes the storage of the sequence of random numbers. A primary function of the program memory is to determine when the selector mechanism 50 is to operate. That is, it counts the number of articles 22 which are detected by the sensor 46, then coordinates with the development mechanism section of the micro-computer 36 to arrive at that particular number of the next article 22 to be removed from the conveyor 24. When this is determined, it signals the micro-computer 36 via electrical lead 54 to operate a drive circuit 56 via electrical lead 57. The drive circuit actuates a selector ram 58 which is suitably positioned over the conveyor 24 in the vicinity of the sample collection container 26 to engage an article 22 and cause it to move off the conveyor 24 and into the container 26. The selector ram 58 may be pneumatically operated as by an air cylinder 60 which is fed air from a suitable compressor 62 via a suitable valve 64. Of course, it will be appreciated that the selector ram 58 may be operated electrically, as by a solenoid, or hydraulically, or in some other suitable fashion.

In accordance with the invention, the random sampler 20 is generally as previously described and includes first display means responsive to operation of said first selection means for displaying the total number established for the batch of the articles from which the random selection is to be taken. As embodied herein, with reference to FIG. 2, a numerical display 66 is provided in the front panel of the control unit 29 adjacent to the first selector 28. When the thumbwheel switches 30 have been actuated by the operator to denote the number of articles 22 chosen for the batch, such information is then visually displayed on the numerical display 66 in any suitable fashion, there being some appropriate connection between the display 66 and the selector 28, depending upon whether the display 66 is operated mechanically, electrically, electronically, or in some other manner. Correlation between the information presented on the display 66 and entered in the micro-computer 36 is provided by an electrical lead 67.

In accordance with the invention, the random sampler is generally as previously described including second display means responsive to operation of said second selection means for displaying the total number established for samples of the articles to be taken from the batch. As embodied herein, with continued reference to FIG. 2, a numerical display 68 of the number of samples to be chosen is utilized to provide visual information correlating to the information previously applied to the thumbwheel switches 34 by the operator. As in the instance of the numerical display 66, the numerical display 68 is suitably connected to the second selector 32 in such a manner as to reflect the information placed into the system by the operator. Similarly correlation between the information presented on the display 68 and entered in the micro-computer 36 is provided by an electrical lead 69.

In accordance with the invention, the random sampler is generally as previously described wherein said developing means is operable to arrange the random numbers in a sequential fashion. As embodied herein, a preferred function of the program memory 52 is for it to be programmed in such a manner that it operates upon the numbers stored in the random access memory 44 such that they are arranged in a sequential fashion. Thus, the micro-computer 36 is enabled to excite the drive circuit 56 as each successive article 22 to be ejected into the sample collection container 26 arrives at a location opposite the selector mechanism 50.

In accordance with the invention, the random sampler is generally as previously described and includes a third display means responsive to operation of said sensor means and said selection means for displaying the number of articles still to pass the predetermined station immediately prior to the next sample scheduled for removal from the advancing series thereof. As embodied herein, with continued reference to FIGS. 2 and 3, a numerical display 70 is also provided in the front panel of the control unit 29. The display 70 is responsive to operation of the sensor 46 and selector mechanism 50 for displaying the number of articles remaining before the next sample is selected, as determined by the random access memory 44, for removal by the selector ram 58. The sensor 46 operates the display 70 after the sampler 20 is placed in operation and after information has been provided to the displays 66 and 68.

Thus, the display 70 is a changing one which counts down as the articles pass, and is then updated with the next random interval immediately after a sample has been taken. For the sake of clarity, consider an example in which the following list of random numbers has been established: 107, 362, 753, etc. When the reset button 42 was pressed, these were the numbers which were generated. Before the first article passes the sensor 46, the display 70 will read "107", which is the interval before the first sample. After the first article passes the sensor 46, the display 70 will read "106", then "105" after the second article, and so on. When the display 70 reads "0", the first sample is taken from the conveyor 24, at which point, the display 70 is updated to read "255". It should be noted that "255" is the interval to the next sample (i.e. 362−107). The process is repeated; as article number 362 is selected to become the second sample, the display 70 is updated to read "391" (i.e. 753−362), and so on. In this manner, an observer is informed that the random sampler 20 is truly operative when it is between samples being taken and to provide reassurance that, indeed, a sample will be taken before long. Of course, the declining count presented on the display 70 informs the observer just how soon the next sample will actually be taken.

The program memory 52 also cooperates by organizing into numerical sequence the output of information to the display 70 at the appropriate time. As with the displays 66 and 68, the particular form of the display is not essential to the invention but may be of any suitable form adequate for the purpose. Similarly with the displays 66 and 68, correlation between the information presented on the display 70 and entered in the micro-computer 36 is provided by an electrical lead 71.

In accordance with the invention, the random sampler is generally as previously described wherein said selection means includes a counter responsive to operation of said sensor means for counting the number of articles which has been removed from the advancing series thereof since the beginning of the batch; and display means responsive to said counter for displaying such information. As embodied herein, the micro-computer 36 includes a counter section which is responsive to the article sensor 46 and to the selector mechanism 50 for counting the number of articles which has been ejected from the conveyor 24 into the sample selection container 26. As that process continues, the micro-computer then instructs a suitable display 72 to present a visual representation of the number of samples already received within the container 26. Similarly with the displays 66, 68, and 70, correlation between the information presented on the display 70 and entered in the micro-computer 36 is provided by an electrical lead 73.

Figure 4:
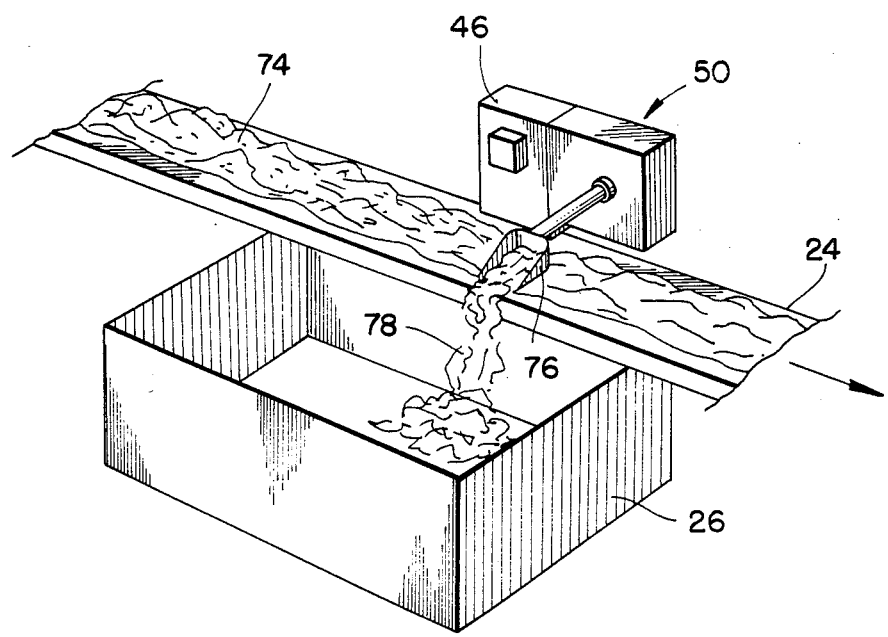
FIG. 4 is a perspective view, similar to FIG. 1, but illustrating a modified sampling system which operates to take random samples of fungible material as it advances on the conveyor.

The preceding description has been limited to a discussion of the random sampling of finite articles 22. It will be appreciated, however, that it is highly desirable as well to sample quantities of material which are of a fungible nature: that is, material which is not neatly packaged in boxes, cans, bottles, or other containers, but rather may be in an unpackaged form. Such fungible material would customarily be particulate in form, or liquid, that is, of such a nature that one specimen or part cannot be distinguished from another specimen or part. For sampling of such fungible material, attention is directed to FIG. 4 which illustrates a system much similar to FIG. 1 except that the conveyor 24 is shown carrying such fungible material 74 as it advances past the sample collection container 26. The selector mechanism 50 may be as previously described except that in place of the plunger 58, a scoop 76 is provided to discharge sample quantities 78 into the container 26. Furthermore, the sensor 46 may be of a nature that it senses incremental advancement of the fungible material 74 as a function of time lapse since the beginning of the batch from which the random selection is to be taken. In another instance, the incremental advancement may be a function of cumulative weight of the fungible material moved since the beginning of movement of the batch from which the random selection is to be taken. In yet another instance, the incremental advancement might be a function of the cumulative distance moved by the fungible material since the beginning of movement of the batch from which the random selection is to be taken.

In any event, other than as just mentioned, the operation of the random sampling system would be in all respects the same as that already described with respect to the sampling of finite samples utilizing the disclosure presented in FIGS. 2 and 3.

While the preferred embodiments of the invention have been disclosed in detail, it should be understood by those skilled in the art that various modifications may be made to the illustrative embodiments without departing from the spirit and the scope thereof as described in the specification and defined in the appended claims.

I claim:

1. Apparatus for randomly selecting articles for removal from an advancing series thereof as they pass a predetermined station comprising:
   first selection means operable for establishing the total number of a batch of the articles from which the random selection is to be taken;
   second selection means operable for establishing the total number of samples of the articles to be taken from the batch;
   a number generator providing a very long sequence of numbers;
   reset means operable to externally interrupt said number generator to establish a starting point in the sequence of numbers provided by said number generator;
   developing means responsive to operation of said reset means for developing a series of random numbers within the magnitude of the batch size as established by said first selection means, each random number representing an incremental advancement of the series of articles;
   random access memory means for storing in memory the series of numbers developed by said developing means;
   sensor means for sensing the presence of each of the articles as it passes a predetermined station; and
   selection means operable for removing from the advancing series of articles these articles which relate in the sequence to each randomly generated number stored within said random access memory means.

2. Apparatus as set forth in claim 1 including first display means responsive to operation of said first selection means for displaying the total number established for the batch of the articles from which the random selection is to be taken.

3. Apparatus as set forth in claim 1 including second display means responsive to operation of said second selection means for displaying the total number established for samples of the articles to be taken from the batch.

4. Apparatus as set forth in claim 1 wherein said developing means is operable to arrange the random numbers in a sequential fashion.

5. Apparatus as set forth in claim 1 including third display means responsive to operation of said sensor means and said selection means for displaying the number of articles still to pass the predetermined station immediately prior to the next sample scheduled for removal from the advancing series thereof.

6. Apparatus as set forth in claim 1 wherein said selection means includes a counter responsive to operation of said sensor means for counting the number of articles which has been removed from the advancing series thereof since the beginning of the batch; and display means responsive to said counter for displaying such information.

7. Apparatus for randomly removing sample quantities from an advancing flow of fungible material as such fungible material passes a predetermined station comprising:
   first selection means operable for establishing the total magnitude as a batch of the fungible material from which the random selection is to be taken;
   second selection mean operable for establishing the total number of samples of the fungible material to be taken from the batch;
   a number generator providing a very long sequence of numbers;
   reset means operable to externally interrupt said number generator to establish a starting point in the sequence of numbers provided by said number generator;
   developing means responsive to operation of said reset means for developing a series of random numbers within the magnitude of the batch size as established by said first selection means, each random number representing an incremental advancement of the fungible material;

random access memory means for storing in memory the series of numbers developed by said developing means;

sensor means for determining the extent of the advancement of the fungible material past the predetermined station; and selection means operable for removing at predetermined intervals from the advancing flow of fungible material sample quantities which relate in the sequence to each randomly generated number stored within said random access memory means.

8. A process of randomly selecting articles for removal from an advancing series thereof comprising the steps of:

($a_1$) establishing the total number of a batch of the articles from which the random selection is to be taken;

($b_1$) establishing the total number of samples of the articles to be taken from the batch;

($c_1$) externally interrupting a number generator providing a very long sequence of numbers to establish the starting point in a sequence of random numbers;

($d_1$) developing from the sequence of numbers beginning with the starting point as obtained in step ($c_1$), a series of random numbers while the magnitude of the batch equal to the total number of samples as established in step ($b_1$), each random number representing an incremental advancement of the series of articles;

($e_1$) storing in memory the series of random numbers developed in step ($d_1$);

($f_1$) sensing the presence of each of the articles as it passes a predetermined station; and ($g_1$) selecting for removal from the advancing series of articles those articles which relate in the sequence to each randomly generated number stored in memory in step ($e_1$).

9. A process as set forth in claim 8 wherein the step ($e_1$) of storing in memory the series of random numbers generated in the previous step ($d_1$) is performed in a sequential fashion.

10. A process as set forth in claim 8 wherein the incremental advancement recited in step ($d_1$) is a function of the number of articles which have passed the predetermined station since the occurrence of step ($g_1$) for the immediately preceding sample article.

11. A process as set forth in claim 8 wherein the incremental advancement recited in step ($d_1$) is a function of the number of articles which have passed the predetermined station in step ($f_1$) since the beginning of the batch from which the random selection is to be taken.

12. A process as set forth in claim 8 comprising the additional steps of:

($h_1$) displaying the number of the batch according to the number established in step ($a_1$); and ($i_1$) displaying the total number of samples to be taken from the batch according to the numbers established in step ($b_1$).

13. A process as set forth in claim 8 comprising the additional steps of:

($j_1$) displaying a number which identifies the next sample to be taken in the process; and ($k_1$) changing the number displayed to reflect the current situation as each sample is removed from the advancing series thereof.

14. A process as set forth in claim 8 comprising the additional step of:

($l_1$) removing from the advancing series of articles each sample article sequentially selected for removal therefrom.

15. A process of randomly removing sample quantities from an advancing flow of fungible material comprising the steps of:

($a_2$) establishing the total magnitude as a batch of the fungible material from which the random selection is to be taken;

($b_2$) establishing the total number of samples of the fungible material to be taken from the batch;

($c_2$) externally interrupting a number generator providing a very long sequence of numbers to establish the starting point in a sequence of random numbers;

($d_2$) developing from the sequence of numbers beginning with the starting point as obtained in step ($c_2$), a series of random numbers within the magnitude of the batch equal to the total number of sample quantities as established in step ($b_2$), each random number representing an incremental advancement of the fungible material;

($e_2$) storing in memory the series of random numbers generated in step ($d_2$);

($f_2$) sensing the advancement of the fungible material at a predetermined station; and ($g_2$) selecting for removal at predetermined intervals from the advancing flow of fungible material sample quantities which relate in the sequence to each randomly generated number stored in memory in step ($e_2$).

16. A process as set forth in claim 15 wherein the step ($e_2$) of storing in memory the series of random numbers generated in the previous step ($d_2$) is performed in a sequential fashion.

17. A process as set forth in claim 15 wherein the total quantity recited in step ($a_2$) is a function of time and wherein the incremental advancement recited in step ($d_2$) is a function of time lapse since the beginning of movement of the batch from which the random selection is to be taken.

18. A process set forth in claim 15 wherein the total quantity recited in step ($a_2$) is a function of time and wherein the incremental advancement recited in step ($d_2$) is a function of time lapse since the occurrence of step ($g_2$) for the immediately preceding sample quantity.

19. A process as set forth in claim 15 wherein the total quantity recited in step ($a_2$) is a function of weight of the fungible material and wherein the incremental advancement recited in step ($d_2$) is a function of cumulative weight of the fungible material moved since the beginning of movement of the batch from which the random selection is to be taken.

20. A process as set forth in claim 17 wherein the total quantity recited in step ($a_2$) is a function of weight of the fungible material and wherein the incremental advancement recited in step ($d_2$) is a function of weight of the fungible material moved since the occurrence of step ($g_2$) for the immediately preceding sample quantity.

21. A process as set forth in claim 15 wherein the total quantity recited in step ($a_2$) is a function of distance of movement of the fungible material and wherein the incremental advancement recited in step ($d_2$) is a function of cumulative distance moved by the fungible material since the beginning of movement of the batch from which the random selection is to be taken.

22. A process as set forth in claim 19 wherein the total quantity recited in step ($a_2$) is a function of distance of movement of the fungible material and wherein the incremental advancement recited in step ($d_2$) is a function of distance moved by the fungible material since the occurrence of step ($g_2$) for the immediately preceding sample quantity.

* * * * *